United States Patent [19]

McFarlane et al.

[11] 4,455,298

[45] Jun. 19, 1984

[54] PHARMACEUTICAL PREPARATIONS WITH GASTRO-PROTECTIVE ACTION

[76] Inventors: Stuart J. McFarlane, 5 Montmere Ave., Te Atatu; John E. Croft, 23 Waimarie Rd., Whenuapai Village, both of Auckland, New Zealand

[21] Appl. No.: 376,898

[22] Filed: May 10, 1982

Related U.S. Application Data

[63] Continuation of Ser. No. 194,152, filed as a PCT EP 79/00072, Sep. 20, 1979, published as WO 80/00661, Apr. 17, 1980, abandoned.

[30] Foreign Application Priority Data

Sep. 25, 1978 [NZ] New Zealand .................. 188489

[51] Int. Cl.$^3$ ............................................. A61K 35/56
[52] U.S. Cl. ...................................... 424/95; 424/274; 424/275; 424/308; 424/309; 424/317; 424/319
[58] Field of Search ........................................... 424/95

[56] References Cited

PUBLICATIONS

Cullen et al.–New Zealand Med. J., Mar. 12, 1975, pp. 260–261.
Highton et al.–New Zealand Med. J., Mar. 12, 1975, pp. 261–262.

*Primary Examiner*—Sam Rosen
*Attorney, Agent, or Firm*—Joseph G. Kolodny

[57] ABSTRACT

The invention concerns novel pharmaceutical preparations containing (A) an extract of the mollusc *Perna canaliculus*, a mussel which is found on the shores of New Zealand, and (B) a pharmaceutically active substance, especially medicaments having anti-phlogistic, antipyretic and/or analgetic action, which, when taken per se, may cause as a side effect irritation of the gastrointestinal mucosae and possibly the formation of ulcers. The addition of a mollusc extract according to (A) to the said medicaments has a gastro-protective action, in that the occurence of the said side effects is prevented or diminished. The component (A) is preferably used as a dry powder of the whole of the flesh of the mollusc or a dry powder obtained from the gonads thereof. In a typical preparation according to the invention an extract of the gonads is e.g. combined with acetyl-salicylic acid. The preparations may contain the 2 components in one and the same dosage unit form, e.g. a capsule or in 2 different ones, e.g. a capsule and a tablet.

The invention also includes a method for preventing, alleviating or treating gastro-intestinal irritation or ulcer formation by administering an effective amount of the mollusc extract as defined under A.

16 Claims, No Drawings

PHARMACEUTICAL PREPARATIONS WITH GASTRO-PROTECTIVE ACTION

CROSS REFERENCE TO RELATED APPLICATION

This application is a continuation of U.S. patent application Ser. No. 06/194,152 filed as a PCT EP 79/000 72, Sep. 20, 1979, published as WO 80/00661, Apr. 17, 1980, now abandoned, said Ser. No. 06/194,152 having an International Filing Date of Sept. 20, 1979 based on International Application Number PCT/EP 79/00072.

The present invention relates to novel pharmaceutical preparations for oral administration, in particular to pharmaceutical preparations containing (A) an extract of the mollusc *Perna canaliculus,* and (B), a pharmaceutically active substance which may cause irritation to the mucosae of the gastro-intestinal tract, and/or favor the formation of gastro-intestinal ulcers as side effects, and to the use of these preparations for the corresponding indications envisaged for component B, as well as a method of counteracting the irritant or ulcerative effect on the mucosae of the gastro-intestinal tract produced by a pharmacologically active compound as defined under (B) by taking together with such compound simultaneously or in succession a mollusc extract as defined under A.

The invention also provides a method of preventing, alleviating or treating gastro-intestinal irritation conditions, lesions, and/or ulcer formation by administering a mollusc extract as defined under A.

Drugs administered to persons for therapeutic reasons may have amongst their side effects the creation of gastric ulcers and stomach bleeding, which in some cases may be serious and could occasionally even threaten the life of the individual. The object of the present invention is to reduce or prevent the occurrence of such side effects in the stomach or intestine of the person taking such drugs. It has been found that such gastro-protective or anti-ulcer effects can be obtained by the additional intake of an extract from the green-lipped mussel, *Perna Canaliculus,* a mollusc which is indigenous to New Zealand, but which can be raised in special farms on the shores of other places. A mollusc extract as defined under (A) is any product obtainable from the flesh of the animal or its organs and suitable for being used for the preparation of pharmaceutical preparations, and in particular (a) the powder obtained by drying and grinding the whole of the flesh of the mollusc,
(b) the lipid extract mixture obtained by solvent extraction of the flesh of the molluscs or of the dry powder as mentioned under (a),
(c) the powder obtained by drying and grinding the gonads of the mollusc, or
(d) the lipid extract mixture obtained by solvent extraction of the gonads or of the dry powder as mentioned under (c).

The manufacture of these various preparations and extracts can be performed as follows:

with respect to (a):
(1) the outside of the shellfish is washed with high pressure hosing, and
(2) the flesh is removed from the shell, for example, by hand, ensuring that no heat is applied, as the temperature should not exceed 10° C.
(3) The product is tested for bacteria and heavy metal content, as only shellfish can be used which have no such contamination.
(4) The flesh is placed in a grinding machine and pulverized into small pieces, then placed onto trays, preferably having an uniform thickness of about ¾ inch,
(5) and freeze-dried.
(6) The freeze-dried material is then crushed into a fine powder and sealed, preferably into vacuum-packed containers.

With respect to (c): The same procedure is followed as under (a), except that the gonads only are removed and used.

The lipids extract mixtures mentioned under (b) and (d) above can be obtained from the whole of the flesh or the gonads of the mussel by extraction with a suitable organic solvent capable of dissolving lipids, such as a halogenated aliphatic hydrocarbon, for instance, methylene or ethylene chloride, chloroform or carbon tetrachloride, aromatic hydrocarbons, such as benzene, toluene, or the xylenes, or esters, such as ethyl acetate. The extraction can be performed in a manner known per se. The lipid extract mixtures obtained in this manner can be used directly for grinding, if the organic solvent extract has been suitably dried before being evaporated. Alternatively the dry extracts as described under (a) and (c) can be used for extraction with the said organic solvent.

A mollusc extract as indicated under (c) is available on the market as a commercial product under the brand name "Seatone" and is sold in pharmacies and health food stores e.g. in a number of countries, such as Canada, Australia, New Zealand, United Kingdom, Switzerland, Holland and Denmark, and is supplied by McFarlane Laboratories Ltd., 23/27 Heather Street, Parnell, Auckland N.Z. The substance is sold as a food supplement in the above countries.

The composition of the mussel extract "Seatone" named above is as follows:

| | | |
|---|---|---|
| moisture content: | 0.65%–3.21% | (average = 2.23%); |
| lipid content: | 0.67%–10.54% | (average = 9.09%); |
| protein content: | 52.13%–55.60% | (average = 53.57%); |
| carbohydrate content: | 18.60%–24.29% | (average = 22.25%); and |
| ash content: | 11.7%–14.90% | (average = 12.83%). |

Minerals (average percentages)

| | | |
|---|---|---|
| sodium | = | 3.04% |
| potassium | = | 0.94% |
| magnesium | = | 0.41% |
| calcium | = | 0.49% |
| zinc | = | 0.01% |
| copper | = | 0.00062% |
| cadmium | = | 0.000027% |
| lead | = | 0.00016% |
| maganese | = | 0.00116% |
| iron | = | 0.04% |
| mercury | = | 0.0000196% |
| nickel | = | 0.0006% |
| selenium | = | 0.000145%. |

In terms of amino acids the composition of the product is as follows:

| Amino acids | % |
| --- | --- |
| Cysteic acid | 3,1 |
| Aspartic acid | 4,9 |
| Threonine | 2,3 |
| Serine | 2,0 |
| Glutamic acid | 6,4 |
| Proline | 2,2 |
| Glycine | 4,2 |
| Alanine | 2,4 |
| Valine | 1,9 |
| ½ Cystine | 0,6 |
| Methionine | 1,1 |
| Iso-Leucine | 1,8 |
| Tyrosine | 1,5 |
| Phenylalanine | 1,8 |
| NH₄ | 0,6 |
| Lysine | 3,2 |
| Histidine | 0,8 |
| Arginine | 3,5 |

"Seatone" and other similar extracts, such as the extracts (a), (b), (c) and (d) named above, obtained from the mollusc *Perna canaliculus* have extremely low toxicity, and there has been no indication of any hazardous side effects and no contra-indication, apart from cases of persons being allergic to shellfish.

The component (B) above can be any pharmacologically active substance which, when taken per os, may cause irritation to the mucosae of the stomach or intestine, and could favor the formation of ulcers. It is especially a substance having anti-phlogistic, anti-pyretic and/or analgesic action, e.g. one of the known substances having these properties. These substances can also be present in the pharmaceutical preparations according to the invention in the form of pharmaceutically acceptable, non-toxic salts such as acid addition salts or salts with bases.

Particularly suitable compounds having antiphlogistic, anti-pyretic and analgesic action are those of the salicyclic acid type and derivatives thereof, especially salicylamide, of the pyrazolinone or pyrazolidinedione type, in particular phenazones, such as propyphenazone or aminophenazone, as well as phenylbutazone or oxyphenbutazone and in addition compounds of the acylaminophenol type and their ethers, of the aryl-lower alkanoic acid and aryl-lower alkenoic acid type, and also of the anthranilic acid type and similar compounds possessing antiphlogistic, antipyretic and analgesic properties, or pharmaceutically acceptable, non-toxic salts with bases or acid addition salts of such compounds.

Active compounds of the salicylic acid type as defined herein are in particular compounds of the formula

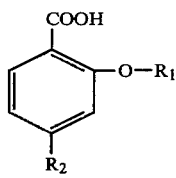

(II)

wherein $R_1$ is hydrogen or acyl, such as lower alkanoyl, e.g. acetyl, and $R_2$ is hydrogen or phenyl which is unsubstituted or substituted e.g. by halogen, such as fluorine, for example 2,4-difluorophenyl, or pharmaceutically acceptable non-toxic salts thereof, as well as carboxylic acid derivatives of such compounds, such as esters and amides. Examples of compounds of this type are carboxylic acids, such as salicyclic acid and O-acetylsalicylic acid, and 4-(2,4-difluorophenyl)-salicylic acid (diflunisal) or pharmaceutically acceptable non-toxic salts thereof, furthermore esters, such as 4-acetylaminophenyl O-acetylsalicylate (benorylate), and 3-phenylpropylsalicylate, and amides, in particular salicylamide.

Compounds of the pyrazolinone type having antiphlogistic, antipyretic and analgesic action are in particular those of the formula

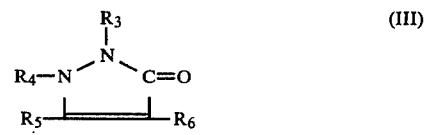

(III)

wherein $R_3$ is a substituted or unsubstituted carbocyclic or heterocyclic radical of aromatic character, especially phenyl, $R_4$ and $R_5$ are lower alkyl, in particular methyl, and $R_6$ is hydrogen, lower alkyl which is unsubstituted or substituted e.g. by a substituted amino group, for example isopropyl, or substituted amino, such as lower alkylamino, di-lower alkylamino, acylamino, N-acyl-N-lower alkylamino, N-(sulfomethyl)amino or N-(sulfomethyl)-N-lower alkylamino. Representatives of this type of compound having antiphlogistic, antipyretic and analgesic action are 2,3-dimethyl-4-isopropyl-1-phenyl-3-pyrazolin-5-one (propyphenazone), 2,3-dimethyl-4-(dimethylamino)-1-phenyl-3-pyrazolin-5-one (aminophenazone), 2,3-dimethyl-1-phenyl-3-pyrazolin-5-one (antipyrin), 2,3-dimethyl-4-(N-methyl-N-nicotinoyl-amino)-1-phenyl-3-pyrazolin-5-one (methylnifenazine), sodium salts of (N-antipyrinylamino)-methansulfonic acid (melansulfone) and of (N-antipyrinyl-N-methyl-amino)-methanesulfonic acid [dipyrone (BAN, USAN)], or 2,3-dimethyl-4-C-[4-N-(6-methoxy-3-pyridazinyl)-sulfamoyl]-anilino]-sulfomethyl-1-phenyl-3-pyrazolin-5-one (sufenazone).

Compounds of the pyrazolidinedione-type having antiphlogistic properties are particularly those of the formula

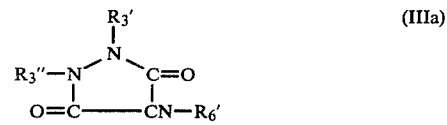

(IIIa)

wherein each of $R_3'$ and $R_3''$ is a carbocyclic radical of aromatic character, such as optionally substituted phenyl, containing as substituent, for example, hydroxy, and $R_6'$ is optionally substituted lower alkyl, containing as substituent, for example, oxo. Representative members of this group of compounds are, for example, 1,2-diphenyl-4-n-butyl-pyrazolidin-3,5-dione (phenylbutazone) and 1-(4-hydroxyphenyl)-2-phenyl-4-n-butyl-pyrazolidine-3,5-dione (oxyphenbutazone).

Compounds of the acylaminophenol type as defined herein are in particular compounds of the formula

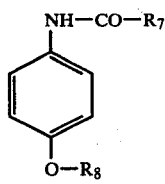

(IV)

wherein $R_7$ is lower alkyl which is unsubstituted or substituted e.g. by hydroxyl, for example methyl or 1-hydroxyethyl, and $R_8$ is hydrogen or lower alkyl. Compounds of this type are, inter alia, N-acetyl-4-ethoxy-aniline (phenacetin), 4-ethoxy-N-(2-hydroxy-propionyl)-aniline (lactophenin) oder 4-acetylamino-phenol (paracetamol).

Compounds of the anthranilic acid type as defined herein are e.g. compounds of the formula

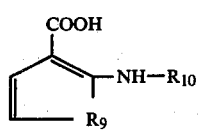

(V)

wherein $R_9$ is the group of the formula —CH=CH—, —S— or —CH=N—, and $R_{10}$ is phenyl which is unsubstituted or substituted by lower alkyl, e.g. methyl, halogen, e.g. chlorine, and/or trifluoromethyl, or is quinolinyl which is unsubstituted or substituted by halogen, e.g. chlorine, and/or trifluoromethyl, for example corresponding 4-quinolinyl, or pharmaceutically acceptable non-toxic salts thereof or esters, for example lower alkyl esters of such compounds which are unsubstituted or substituted by hydroxyl, lower alkoxy, e.g. methoxy or ethoxy, or lower alkanoyloxy, e.g. acetyloxy. Representatives of this class of active compounds as defined herein are e.g. N-(3-trifluoromethylphenyl)-anthranilic acid (flufenamic acid), N-(2,3-dimethyl-phenyl)-anthranilic acid (mefenamic acid), N-(3-chloro-2-methyl-phenyl)-anthranilic acid (tolfenamic acid), N-(2,6-dichloro-3-methyl-phenyl)-anthranilic acid (meclofenamic acid), 2-(3-trifluoromethyl-anilino)-nicotinic acid (niflumic acid), 2-(2,3-dimethyl-anilino)-nicotinic acid, 2-(3-chloro-2-methyl-anilino)-nicotinic acid (clonixin oder clonixidine), 2-(2-methyl-3-trifluoromethyl-anilino)-nicotinic acid (flumixin), N-(2,6-dichloro-3-methyl-phenyl)-anthranilic acid ethoxymethyl ester (etoclofen), 4-(2-chloro-3-methyl-anilino)-3-thiophenecarboxylic acid acetyloxymethyl ester (aclantate), N-(8-trifluoromethyl-4-quinolinyl)-anthranilic acid 2,3-dihydroxy-propyl ester (floctafenine), N-(7-chloro-4-quinolinyl)-anthranilic acid 2,3-dihydroxy-propyl ester (glaphenine), 2-(3-chloro-2-methyl-anilino)-nicotinic acid 2,3-dihydroxypropyl ester (clonixeril) or 4-(8-trifluoromethyl-4-quinolinylamino)-3-thiophenecarboxylic acid 2,3-dihydroxy-propyl ester, and pharmaceutically acceptable non-toxic salts thereof.

In active arylalkene- or arylalkenecarboxylic acid compounds as defined herein, aryl is in particular a preferably substituted carbocyclic hydrocarbon radical of aromatic character; but it can also be a substituted or unsubstituted heterocyclic radical of aromatic character. Preferably, aryl-lower alkanecarboxylic acid compounds are substituted phenylalkanecarboxylic acid compounds of the formula

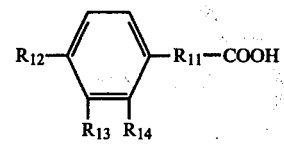

(VI)

wherein $R_{11}$ is in particular lower alkylidene and most preferably methylene or ethylidene, and also propylidene, or lower alkylene or lower alkenylene which is unsubstituted or substituted e.g. by oxo, for example 1-oxo-1,3-propylene, $R_{12}$ is hydrogen, lower alkyl, e.g. isobutyl, cycloalkyl or cycloalkenyl, for example cyclohexyl or 1-cyclohexenyl, unsubstituted or substituted phenyl, lower alkoxy or lower alkenyloxy, e.g. n-butyloxy or allyloxy, lower alkyleneamino or lower alkenyleneamino which is unsubstituted or substituted e.g. in the aliphatic moiety by oxo or lower alkyleneamino or lower alkenyleneamino which contains a fused benzo moiety, e.g. 3-pyrrolin-1-yl or 1-oxo-2-isoindolinyl, or acyl, such as aroyl, wherein aryl is a substituted or unsubstituted carbocyclic hydrocarbon radical of aromatic character or a heterocyclic radical of aromatic character, e.g. thenoyl, $R_{13}$ is hydrogen, halogen, e.g. chlorine, aryloxy, wherein aryl is preferably a substituted or unsubstituted carbocyclic hydrocarbon radical of aromatic character, e.g. phenyloxy, or acyl, in particular aroyl, wherein aryl is preferably a carbocyclic hydrocarbon radical of aromatic character which is unsubstituted or substituted e.g. by halogen, such as chlorine, for example benzoyl or 4-chlorobenzoyl, and $R_{14}$ is hydrogen, lower alkyl, for example methyl, or is phenyloxy which is unsubstituted or substituted e.g. by halogen, such as chlorine, for example 2,4-dichlorophenyloxy, amino or anilino which is unsubstituted or substituted e.g. by halogen, such as chlorine, for example 2,6-dichloroanilino, with the proviso that at least one of the groups $R_{12}$, $R_{13}$ and $R_{14}$ is hydrogen and at least one of them is different from hydrogen, or pharmaceutically acceptable non-toxic salts of such compounds, and also carboxylic acid derivatives, for example esters, such as lower alkyl esters which are unsubstituted or substituted by hydroxyl or etherified hydroxyl, or hydroxamic acids thereof. Representatives of these compounds possessing antiphlogistic properties are, inter alia, 2-(4-isobutyl-phenyl)-propionic acid (ibuprofen), 2-(4-n-butyloxy-phenyl)-acetohydroxamic acid (butexamac), 2-(4-allyloxy-3-chloro-phenyl)-acetic acid (alclofenac), 2-(4-biphenylyl)-butyric acid (buticiclate), 2-[3-(4-chlorobenzoyl)-2-methyl-phenyl]-acetic acid 2,3-isopropylidenedioxy-propyl ester, 2-[4-(2-thenoyl)-phenyl]-propionic acid (suprofen), 2-[3-benzoyl-phenyl]-propionic (ketoprofen), 2-(3-phenyloxy-phenyl)-propionic acid (fenoprofen), 4-(3-chloro-4-cyclohexyl-phenyl)-4-oxo-butyric acid, 2-[4-(1-oxo-2-isoindolinyl)-phenyl]-propionic acid (indoprofen), 2-[4-(3-pyrrolin-1-yl)-phenyl]-propionic acid (pirprofen), 2-(2-amino-3-benzoyl-phenyl)-acetic acid, 2-[2-amino-3-(4-chlorobenzoyl)-phenyl]-acetic acid, 2-[2-(2,4-dichlorophenyloxy)-phenyl]-acetic acid (fenclofenac) or 2-[2-(2,6-dichloroanilino)-phenyl]-acetic acid (diclofenac), or pharmaceutically acceptable salts of such compunds.

A further group of aryl-lower alkanecarboxylic acid and aryl-lower alkenecarboxylic acid compounds comprises those of the formula

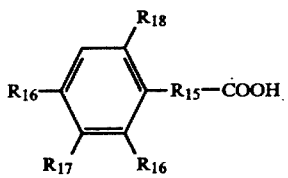

VII

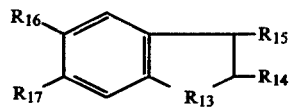

V wherein $R_{15}$ is in particular lower alkylidene and most particularly methylene and ethylidene, or is lower alkylene or lower alkylidene which is unsubstituted or substituted e.g. by oxo, and one of the groups $R_{16}$ is hydrogen and the other together with $R_{17}$ forms a cycloaliphatic, aromatic or heterocyclic ring which is unsubstituted or substituted e.g. by lower alkyl, such as methyl, lower alkoxy, such as methoxy, halogen, such as chlorine, oxo, or by phenyl which is unsubstituted or substituted e.g. by halogen, such as chlorine, and which can contain a fused cycloaliphatic, aromatic or heterocyclic ring, and $R_{18}$ is hydrogen or halogen, e.g. chlorine, or pharmaceutically acceptable non-toxic salts of such compounds. Examples of active compounds of this kind as defined herein are 2-(10-methyl-2-phenothiazinyl)-acetic acid (methiazinic acid), 2-(7-methoxy-10-methyl-2-phenothiazinyl)-propionic acid (proctizinic acid), 2-(6-methoxy-2-naphthyl)-propionic acid (naproxen), 2-[2-(4-chlorophenyl)-5-benzoxazolyl]-propionic acid (benzoxaprofen), 2-(2-phenyl-5benzthiazolyl)-acetic acid, 2-(2-phenyl-5-benzthiazolyl)-propionic acid 2-(7-fluorenyl)-propionic acid (cicloprofen), 2-(11-oxo-2-dibenzoxepinyl)-acetic acid, 2-(2-chloro-4,5-isopropylidenedioxyphenyl)-acetic acid, 2-(3-phenyl-7-benzofuranyl)-propionic acid, 2-(5,6,7,8-tetrahydro-2-carbazolyl)-acetic acid, 2-(6-carbazolyl)-propionic acid, 2-(1-chloro-6-carbazolyl)-propionic acid, 2-(9-oxo-2-xanthenyl)-propionic acid, 4-(2-dibenzofuranyl)-4-oxo-butyric acid (furobufen) or 2-(5H-[1]benzopyrano[2,3-b]pyrid-7-yl)-propionic acid or pharmaceutically acceptable non-toxic salts of such compounds.

A further group of aryl-lower alkanecarboxylic acid or aryl-lower alkenecarboxylic acid compounds, wherein aryl denotes a heterocyclic group of aromatic character, comprises compounds of the formula $$Ar_1—R_{19}—COOH \qquad (VIII)$$

wherein $Ar_1$ is a monocyclic aza-, thia-, thiaza- or oxazacyclic radical of aromatic character which is unsubsituted or substituted e.g. by lower alkyl, such as methyl, phenyl which is unsubstituted or substituted e.g. by halogen, such as chlorine, or acyl, such as benzoyl which is unsubstituted or substituted by lower alkyl, such as methyl, and $R_{19}$ is lower alkylidene, e.g. methylene or ethylidene, and also lower alkylene or lower alkenylene, or pharmaceutically acceptable non-toxic salts thereof. Examples of such compounds are, inter alia, 2-[1-methyl-5-(4-methylbenzoyl)-2-pyrrolyl]-acetic acid (tolmetin), 2-[1-(4-chlorophenyl)-2,5-dimethyl-3-pyrrolyl]-acetic acid (clopirac), 2-(5-benzoyl-2-thienyl)-propionic acid (thiaprofenic acid), 2-(4,5-diphenyl-2-oxazolyl)-propionic acid (oxaprozin), 2-[4-(4-chlorophenyl)-5-thiazolyl]-acetic acid, 2-[2-(4-chlorophenyl)-4-thiazolyl]-acetic acid (fenclozinic acid), 3-[2-(4-chlorophenyl)-4-thiazolyl]-acrylic acid or 2-[3-(4-chlorophenyl)-2-phenyl-5-thiazolyl]-acetic acid (fentiazac).

A further group of aryl-lower-alkane- or aryl-lower-alkene carboxylic acids are those of the formula wherein $R_{13}$ is a methylene group, which may optionally be substituted, e.g. by an aralkylidene group, e.g. 4-methylsulfinyl-benzylidene, or a nitrogen or sulfur atom which may optionally be substituted by an aroyl-, aryl lower alkanoyl- or aryl lower alkenoyl group, e.g. 4-chlorobenzoyl or 3,4-methylenedioxy-benzoyl, one of the groups $R_{14}$ and $R_{15}$ represents the residue of the formula —$(CH_2)_{0,1}$—COOH and the other hydrogen or lower alkyl, especially methyl, and in which preferably at least one of the groups $R_{16}$ and $R_{17}$ represents a substituent, e.g. cycloalkyl, e.g. cyclohexyl, lower alkoxy, e.g. methoxy, halogen, e.g. chlorine, or acyl, such as e.g. benzoyl containing halogen, e.g. chlorine, e.g. benzoyl or 2-chloro-benzoyl, while the other may represent hydrogen or a substituent, for instance hydroxy or halogen, e.g. chlorine, there being optionally present in the five-membered ring between the C-atoms 2 and 3 a double bond, or pharmaceutically acceptable non-toxic salts of such compounds, and acid derivatives thereof, for instance the corresponding amides, e.g. the glucosamides or tetrazole compounds. As examples of this group of compounds there are to be mentioned among others: 2-[1-(4-chloro-benzoyl)-5-methoxy-2-methyl-3-indolyl] acetic acid (indomethacine) 5-cyclohexyl-1-indane carboxylic acid, 6-chloro-5-cyclohexyl-1-indane carboxylic acid, 1-(4-chloro-benzoyl)-3-(5-tetrazolylmethyl)-indole (intrazole), 2-(1-cumaramoyl-5-methoxy-2-methyl-3-indolyl) acetic acid (cinmetazine), 2-[5-methoxy-2-methyl-1-(3,4-methylenedioxy-benzoyl)-3-indolyl]-acetic acid, 2-(5-chloro-3-methyl-2-benzothienyl)-acetic acid, 2-[5-fluoro-2-methyl-1-(4-methylsulfinyl-benzylidene)-3-indenyl] acetic acid (sulindac) and 2-[1-(4-chlor-benzoyl)-5-methoxy-2-methyl-3-indolyl]-acetic acid-glucoseamide (indosamide) or pharmaceutically acceptable, non toxic salts of these compounds.

Suitable salts of the above mentioned compounds, and also of those referred to hereinafter, with basic properties, are pharmaceutically acceptable non-toxic acid addition salts with inorganic acids, for example hydrochloric, hydrobromic, nitric, sulfuric or phosphoric acids, or with organic acids, such as organic carboxylic acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-amino-salicylic acid, 2-phenoxybenzoic acid, 2-acetoxybenzoic acid, embonic acid, nicotinic acid or isonicotinic acid, or organic sulfonic acids, for example methanesulfonic acid, ethanesulfonic acid, 2-hydroxyethanesulfonic acid, ethane-1,2-disulfonic acid, benzenesulfonic acid, 4-methylbenzenesulfonic acid or naphthalene-2-sulfonic acid.

Salts of the above compounds with acid properties are in particular metal or ammonium salts, such as alkali metal salts and alkaline earth metal salts, for example sodium, potassium, magnesium or calcium salts, and ammonium salts with ammonia or suitable organic amines. Suitable amines for the salt formation are in particular aliphatic, cycloaliphatic, cycloaliphatic-aliphatic or araliphatic primary, secondary or tertiary mono-, di- or polyamines, and also heterocyclic bases, such as lower alkylamines, for example triethylamine, hydroxy-lower alkylamines, e.g. 2-hydroxyethylamine, bis-(2-hydroxyethyl)amine or tris-(2-hydroxyethyl)amine, and basic aliphatic esters of carboxylic acids, e.g. 4-aminobenzoic acid 2-diethylamino-ethyl ester, lower alkylene amines, e.g. 1-ethylpiperidine, cycloalkylamines, e.g. dicyclohexylamine, or benzylamines, e.g. N,N'-dibenzylethylenediamine, as well as bases of the pyridine type, e.g. pyridine, collidine or quinoline.

The compounds mentioned above and hereinafter which contain centres of asymmetry can be employed in the form of racemates or of optically active antipodes, or in the case of diastereomerism, also in the form of racemate mixtures.

The dose of the component B having antiphlogistic, antipyretic and analgesic action varies greatly. Thus compounds of the salicylic acid type, i.e. those of the formula II, for example salicylamide or acetylsalicylic acid, can be administered to warm-blooded animals having a body weight of about 60 to 70 kg. e.g. in single doses of about 25 to 250 mg (in daily doses of about 50 to about 1500 mg), compounds of the pyrazolinone type, i.e. those of the formula III, e.g. 2,3-dimethyl-4-isopropyl-1-phenyl-3-pyrazolin-5-one (propyphenazone) or 2,3-dimethyl-4-(dimethylamino)-1-phenyl-3-pyrazolin-5-one (aminophenazone) in single doses of about 25 mg to about 250 mg (in daily doses of about 50 to about 500 mg), compounds of the acylaminophenol type, i.e. those of the formula IV, in single doses of about 200 to about 600 mg (in daily doses of about 400 mg to about 1500 mg), compounds of the anthranilic acid type, i.e. those of the formula V, in single doses of about 25 mg to about 250 mg (in daily doses of about 50 mg to about 500 mg), and compounds of the arylalkane- or arylalkenecarboxylic acid type, i.e. those of the formulae VI to VIII, in single doses of about 50 mg to about 500 mg (in daily doses of about 150 mg to about 1500 mg).

The preferred single doses to be administered to a warm-blooded animal having a body weight of about 60 to 70 kg, for instance for the compounds diclofenac sodium and phenylbutazone are 25–100 mg and 75–200 mg respectively, whereas the daily doses are 100–200 mg and 200–600 mg respectively.

The ratio in weight between the component (A) in the form of an extract (a) or (c) as defined above and the component (B) in the pharmaceutical preparations according to the invention can vary within wide limits, but a range between 1:1 and 50:1 is preferred, especially between 4:1 and 20:1. A ratio of approximately 10:1 is particularly recommended. Naturally, the higher the proportion of mollusc extract to component A is, the greater the gastro-protective effect of the mixture.

The lipid fraction (b) and (d) are up to about 8–10 percent by weight of the extract (a) and (c). Therefore, if component B is being mixed with the lipid fractions (b) or (d), the ratio A to B should be commensurate with those expressed above for the mollusc extract.

In the pharmaceutical preparations according to the present invention the two components A and B can both be present as a mixture in one and the same dosage unit form e.g. in a tablet or capsule, however, they can also be in the form of two dosage unit forms for each of the components A and B, to be taken at the same time.

The dosage of the unit forms of the new preparations depends on the particular component B used. Preferably it is the same as that currently used for the particular, pharmaceutically active compound, when taken alone, but it can be also an aliquot or a multiple of it, depending on the circumstances, e.g. it can be about half or a third or a fourth of the dose normally used.

In addition to the components A and B, the preparations of the present invention normally contain suitable carriers and adjuncts which assist the incorporation of the active components into the preparations. The preparations can be for instance in the form of tablets, film coated tablets, sugar coated tablets or capsules, or as suspensions in containers, such as bottles or plastics, the content of active ingredient being of about 10%–100%. In the solid forms, e.g. those named above, the carriers can be the same as those occuring in the known preparations containing active compounds corresponding to the component B, the ratio of active substance to carrier being the same, and the amount of active substance being the sum of the components A and B, but it can also vary widely from this ratio within the range given above. Preferably the content of active substance in the new preparations is about 20%–about 100%, in particular about 50%–to about 90%.

Suitable carriers are in particular fillers, such as sugar, for example, lactose, saccharose, mannitol or sorbitol, cellulose preparations and/or calcium phosphates, e.g. tricalcium phosphate or calcium hydrogen phosphates, also binders such as starch pastes, for example maize, corn, rice or potato starch paste, gelatin, tragacanth, methyl cellulose, hydroxypropylmethylcellulose, sodium carboxymethylcellulose and/or polyvinylpyrrolidone, and/or, if desired, disintegrators, such as the above starches, also carboxymethyl starch, cross-linked polyvinylpyrrolidone, agar, alginic acid or a salt thereof, such as sodium alginate. Adjuncts are chiefly glidants and lubricants, for example silicic acid, talc, stearic acid or salts thereof, such as magnesium stearate or calcium stearate, and/or polyethylene glycol or fatty substances such as hydrogenated cotton oil. Sugar-coated tablet cores are provided with suitable coatings that can be resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations, such as acetylcellulose phthalate or hydroxypropylmethylcellulose phthalate. By incorporating one or more active components into a suitable carrier which effects a slow release of the active component or components, it is possible to prolong the action of one or more components which in themselves have an action of short duration. Dyes or pigments can be added to the tablets or sugar-coated tablet cores, for example to identify or indicate different combinations of doses of the active components.

Further pharmaceutical preparations for oral administration are dry-filled capsules, and also soft sealed capsules made from gelatin and a plasticiser, such as glycerin or sorbitol. The dry-filled capsules can contain the active ingredient in the form of granules, for example in admixture with fillers such as maize starch, binders and/or lubricants, such as talc or magnesium stearate, and optionally stabilisers. In soft capsules, the active components are preferably dissolved or suspended in suitable liquids, for example in fatty oils, paraffin oil or liquid polyethylene glycols, to which stabilisers, e.g. lecithins, can also be added.

The pharmaceutical preparations of the invention may also include besides the said components (A) and (B) and the pharmaceuticals carriers mentioned other pharmaceutically active compounds, such as vitamins, or compounds having a protective action on the mucosae of the gastrointestinal tract, such as oxides or hydroxides or basic salts of metals like aluminium, magnesium, bismuth, for instance colloidal aluminium trihydroxide or magnesium trisilicate. Vitamin $B_6$ is especially to be mentioned as possible supplementary pharamaceutical contained in the new preparations.

In the case that the pharmaceutical preparations of the present invention are in the form of two separate dosage unit forms for the components A and B, the component A may be in a solid form, e.g. a tablet or capsule, or in liquid form, e.g. as a soft capsule, including a suspension of the mollusc extract, and B may be in any form, according to the nature of the antiphlogistic to be used, e.g. also in solid form or as a suspension or a solution, for instance an aqueous solution e.g. of a soluble metal salt, such as a sodium salt, or in the form of a syrup containing, about 1% to about 12% of the active component.

The pharmaceutical preparations of this invention are prepared in a manner known per se, for example by conventional mixing, granulating, sugar-coating, solution and lyophilising methods. Pharmaceutical preparations which are suitable for oral administration can be obtained by combining the active components with solid carriers, optionally granulating the mixture thereby obtained, and processing the mixture or granules, if desired or necessary after the addition of suitable adjuncts, to tablets or sugar-coated tablet cores.

In particular, for preparing solid forms of the preparations containing the mixture in one single dosage unit form, the component A, in the form of a mollusc extract as mentioned under (a), (b), (c) or (d) above, is mixed in a manner known per se with a solid component B, and the resulting mixture is incorporated in a solid dosage form, for example, a capsule or tablet, for oral administration. In the case that aqueous forms are chosen for the new preparations, either an aqueous solution or a suspension of the component B is mixed with an aqueous suspension of the mollusc extract A and the resulting suspension is filled in suitable containers, for instance, bottles or flasks, or the components A and B are mixed in the solid state and a suitable suspending agent, such as tracaganth, is added, then the required amount of water is added and the suspension filled in the desired containers, or the components A and B are mixed in solid form together with a suspending agent and this solid mixture is filled in suitable containers, the required amount of water being added when the drug is taken by the patient and the container being closed and shaken so as to obtain an uniform suspension.

A second aspect of the present invention is a method for counteracting the irritant or ulcerating side effect of pharmaceutically active compounds on the gastro-intestinal mucosae or for preventing or reducing the formation of gastro-intestinal ulcers consisting in administering concomitantly or in succession with the said pharmaceutically active compound an amount of an extract of the mollusc Perna canaliculus. The mollusc extract is e.g. any of the extracts (a), (b), (c) and (d) named above in relation to the pharmaceutical preparations of the present invention. The pharmaceutically active compound referred to in this method are above all antiphlogistics, antirheumatic or analgesics, especially those reported above. One way to obtain the desired gastro-protective result according to this new method is the administration of any of the pharmaceutical preparations just described. However, the method also envisages the administration of the antiphlogistic and the mollusc extract at different times, in which case the doses to be chosen for the mollusc extract are preferably the same as present in the said pharmaceutical preparations.

Thus an amount varying e.g. from 1 to 50 times the weight of the pharmaceutically active compound, e.g. an antirheumatic, and preferably from 4 to 20 times such weight, of the mollusc extract is employed.

A third aspect of the present invention is a method for preventing, alleviating or treating gastro-intestinal irritation conditions, lesions and/or ulcer formation, consisting in administering to a patient an effective amount of an extract of the mollusc Perna canaliculus.

It has been found that the protective and therapeutical effects on the mucosae of the gastro-intestinal tract of extracts of the New-Zealand green-lipped mussel named above does not ensue only in the presence of a pharmaceutically active compound having an irritant action on the mucosae of the gastro-intestinal tract, but also when taken per se. The said extracts can thus be used as a profilactic or therapeutical agent also in cases where gastro-intestinal irritation conditions or bleeding or ulceration are of other origin than those caused by pharmaceutically active compounds.

Any of the mollusc extracts (a), (b), (c) and (d) described above in relation to the pharmaceutical preparations of the invention can be used according to this new method of prevention or treatment. There is preferably used an extract according to (c), that is an extract of the gonads, or a corresponding lipid fraction according to (d). The doses used may vary within a wide range, the product having a very low degree of toxicity.

The doses may also vary widely according to the necessities and the nature of the disease to be treated. As a rule, the greater the dose is, the greater the anti-irritant or anti-ulcerogenic effect is.

For a mollusc extract of the type (c) above, e.g. for a product having a similar composition as the food-supplement "Seatone", mentioned above, the doses are preferably 200–5000 mg per day for a patient of about 60–70 kg weight. A daily dose range between 280–1000 mg per day is recommended, the treatment being continued for many days until the undesired symptoms disappear. The treatment can then be continued for some time at lower dosage, for instance 200–250 mg per day. The doses to be used for the lipid extracts (b) and (d) mentioned above are correspondingly reduced to about 10% of the doses just mentioned.

The mollusc extracts to be used in the method here described for treating gastro-intestinal ulcers or pre-ulcer-conditions can be in the form of suitable pharmaceutical preparations, similar or equal to those described above for the mixtures of mussels extracts and pharmaceutically active compounds. The dosage unit forms are preferably those corresponding to the daily doses to be administered reported above or aliquots or multiple thereof, e.g. one half to one third of those doses, or especially in the case of the lipids extracts, 2–5 times the quantity of the said doses.

The pharmaceutical preparations of the present invention are suitable for the treatment of the same diseases as envisaged for the medicaments including compounds of the type of component (B), for instance the known antiphlogistics, antipyretics or analgesics named above. As the addition of the mollusc extract [component A] does not impair the therapeutic effect of the said pharmaceutically active compounds and the medicaments containing them, the doses of the active substance of the latter can also be the same in the pharmaceutical preparations of this invention in the form of component B, and such doses can serve as a basis for the manufacture of the new preparations.

The following Examples illustrate the invention, but in no way limit the scope thereof. The temperatures are given in degrees centigrades (Celsius).

EXAMPLE 1

A hard gelatine capsule is filled with 300 mg of O-acetylsalicylic acid mixed with 300 mg of mollusc extract of Perna canaliculus as available in commerce under the trade mark "Seatone" (McFarlane Laboratories Ltd., Auckland, NZ) [designated in the following Examples simply as "Seatone"], 5 mg of magnesium stearate and 50 mg of sodium carboxymethyl starch.

EXAMPLE 2

A hard gelatine capsule is filled with 300 mg of O-acetylsalicylic acid mixed with 300 mg of the lipid fraction obtained by solvent extraction from the product "Seatone", 5 mg of magnesium stearate and 50 mg of sodium carboxymethyl starch.

EXAMPLE 3

A hard gelatine capsule is filled with 25 mg of diclofenac sodium previously granulated with 2.5 mg Polyvinyl pyrrolidone K 30 in ethanol, mixed with 250 mg of "Seatone", 3 mg of magnesium stearate and 100 mg of corn starch.

EXAMPLE 4

A hard gelatine capsule is filled with 50 mg of diclofenac sodium, previously granulated with 5 mg Polyvinylpyrrolidone, mixed with 250 mg of "Seatone", 4 mg of magnesium stearate and 70 mg of corn starch.

EXAMPLE 5

A hard gelatine capsule is filled with 100 mg of phenylbutazone, previously mixed with 50 mg of lactose and 80 mg of corn starch and granulated with 10 mg of Polyvinylpyrrolidone K 30 dissolved in water, and 250 mg of "Seatone" together with 25 mg of talc, 1.5 mg of magnesium stearate and 1.5 mg of colloidal silica.

EXAMPLE 6

A hard gelatine capsule is filled with 100 mg of oxyphenylbutazone, mixed with 100 mg of the lipid fraction obtained from the dried powder of the whole flesh of the mollusc Perna canaliculus together with 25 mg of talc, 1.5 mg of magnesium stearate and 1.5 mg of colloidal silica.

EXAMPLE 7

A hard gelatine capsule is filled with 25 mg of indomethacine, previously mixed with 30 mg of lactose, 20 mg of corn starch and 20 mg of sodium carboxymethylcellulose and granulated with 6 mg of starch past and 2 mg Aerosil 200 (trade mark) (silicagel), mixed with 250 mg of Seatone, 22 mg of cellulose and 5 mg of magnesium stearate.

EXAMPLE 8

A hard gelatine capsule is filled with 50 mg of tolmetin mixed with 250 mg of Seatone and 100 mg of corn starch.

EXAMPLE 9

Hard gelatine capsules of "Seatone" containing a core in form of a tablet including diclofenac sodium.

A hard gelatine capsule containing 250 mg of Seatone is prepared, the core of which capsule is constituted by a tablet containg 25 mg of diclofenac sodium and has the following composition

| | |
|---|---|
| Diclofenac sodium | 25,0 mg |
| Polyvinylpyrrolidon | 2,0 mg |
| Cellulose powder | 7,1 mg |
| Lactose | 20,0 mg |
| Highly dispersed silicim dioxide | 2,0 mg |
| Sodium-carboxymethyl-starch | 16,0 mg |
| Talc | 2,5 mg |
| Magnesium stearate | 1,5 mg |
| Total | 68,0 mg |

EXAMPLE 10

Combination "blister" package containing "Seatone" and—acetyl—salicylic acid.

In a combination blister package each foil contains two rows of different dosage unit forms, one of tablets containing each 300 mg of acetyl salicylic acid (and any of the normal carriers used for tablets) and the other of capsules containing 600 mg of "Seatone".

EXAMPLE 11

Capsule containing 300 mg of a gonad extract of Perna canaliculus having a composition corresponding to the product "Seatone" defined above and prepared as described above.

Such capsule can be taken daily for the treatment of gastro-intestinal irritation or ulcers according to the indications made above.

EXAMPLE 12

Capsule containing a daily dose of 30 mg of a lipids mixture obtained by extracting the product Seatone with an organic lipid solvent, such as carbon tetrachloride or chloroform, for the treatment for gastro-intestinal ailments as indicated in Example 11.

What we claim is:

1. A pharmaceutical preparation for oral administration containing as component A
    (a) the powder obtained by drying and grinding the whole of the flesh of the mollusc Perna canaliculus,
    (b) the lipid extract mixture obtained by solvent extraction of the flesh of the mollusc Perna canaliculus or of the dry powder as defined under (a) with a lipid dissolving organic solvent,
    (c) the powder obtained by drying and grinding the gonads of the mollusc Perna canaliculus, or
    (d) the lipid extract mixture obtained by solvent extraction of the gonads of the mollusc Perna canaliculus or of the dry powder as defined under (c) with a lipid dissolving organic solvent,
and as component B an antiphlogistic, antipyretic or analgesic acting compound of the formula

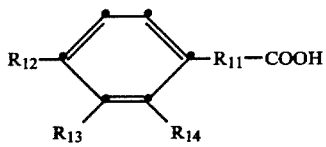

wherein $R_{11}$ is lower alkylidene, or lower alkylene or lower alkenylene which are unsubstituted or substituted by oxo, $R_{12}$ is hydrogen, lower alkyl, cyclohexyl, cyclohexenyl, phenyl, lower alkoxy, lower alkenyloxy, lower alkyleneamino or lower alkenyleneamino which is unsubstituted or substituted by oxo or lower alkyleneamino, 1-oxo-2-isoindolinyl or thenoyl, $R_{13}$ is hydrogen, halogen, phenyloxy or benzoyl which is unsubstituted or substituted by halogen, and $R_{14}$ is hydrogen, lower alkyl, phenyloxy which is unsubstituted or substituted by halogen, amino or anilino which is unsubstituted or substituted by halogen, with the proviso that at least one of the groups $R_{12}$, $R_{13}$ and $R_{14}$ is hydrogen and at least one of them is different from hydrogen, or a pharmaceutically acceptable salt of such a compound, or a lower alkyl ester which is unsubstituted or substituted by hydroxyl, or the hydroxamic acid derivative thereof.

2. A pharmaceutical preparation as claimed in claim 1, wherein component A is the powder obtained by drying and grinding the whole of the flesh of the mollusc Perna canaliculus at a temperature below 10° C.

3. A pharmaceutical preparation as claimed in claim 1, wherein component A is the powder obtained by drying and grinding the gonads of the mollusc Perna canaliculus at a temperature below 10° C.

4. A pharmaceutical preparation as claimed in claim 1, wherein component A is a powder produced from the gonads of the mollusc Perna canaliculus by a process, comprising the steps of:
(1) washing the outside of the shellfish by high pressure hosing,
(2) mechanically removing the flesh from the shell without applying heat and taking care that the temperature does not exceed 10° C.,
(3) testing the product for bacteria and heavy metal content, discarding those shellfish having said contamination,
(4) mechanically separating the gonads from the flesh,
(5) pulverizing the gonads in a grinding machine into small pieces,
(6) freeze drying the small pieces by placing them on trays having uniform thickness of about ¾ inch,
(7) crushing the freeze dried material into fine powder, and finally
(8) sealing the fine powder in vacuum packed containers.

5. A pharmaceutical preparation as claimed in claim 4 wherein component B is diclofenac sodium.

6. A pharmaceutical preparation as claimed in claim 1, wherein component B is diclofenac or a pharmaceutically acceptable salt thereof.

7. Pharmaceutical preparations as claimed in claim 1, wherein the ratio of component A to component B is in the range between 50:1 and 1:1, expressed in parts by weight.

8. Pharmaceutical preparations as claimed in claim 1, wherein the ratio of component A to component B is in the range between 20:1 and 4:1, expressed in parts by weight.

9. Pharmaceutical preparations as claimed in claim 1, wherein the dosage unit form is in the form of a capsule containing both components A and B in solid form together with a pharmaceutical carrier.

10. Pharmaceutical preparations as claimed in claim 1, wherein the dosage unit form is in the form of an aqueous suspension of both components A and B.

11. Pharmaceutical preparations as claimed in claim 1, wherein the dosage unit form is in the form of a capsule containing component A and which capsule has a core in the form of a tablet containing the component B.

12. Pharmaceutical preparations as claimed in claim 1, in form of blister packages containing foils with two rows of unit dosage forms, one containing component A and the other component B.

13. Pharmaceutical preparations as claimed in claim 12, wherein the dosage unit form for A is a capsule and the dosage unit form for B is a tablet.

14. A method for treating gastrointestinal irritation conditions, lesions and ulcer formation consisting in administering to a patient suffering from any of these conditions an effective amount of a pharmaceutical preparation of claim 1.

15. A method as claimed in claim 14, wherein a daily dose of 200 mg–5000 mg of the powder having a composition wherein component A is in capsule form and component B is in tablet form is administered.

16. A method as claimed in claim 14, wherein a daily dose of about 20 mg–500 mg of the lipid extract mixture obtained by solvent extraction of the gonads of the mollusc *Perna canaliculus* or of the dry powder obtained by drying and grinding the gonads of the mollusc Perna canaliculus is administered.

* * * * *

UNITED STATES PATENT AND TRADEMARK OFFICE
CERTIFICATE OF CORRECTION

PATENT NO.  : 4,455,298
DATED       : June 19, 1984
INVENTOR(S) : Stuart J. McFarlane, et al It is certified that error appears in the above-identified patent and that said Letters Patent is hereby corrected as shown below:

| | |
|---|---|
| Under "Foreign Application Priority Data" | Insert --September 19, 1979 European 79810098.8-- |
| Col. 5, line 61 | Delete "arylalkene-" and substitute --arylalkane-- |
| Col. 7, line 29 | After "5" insert -- - -- |
| Col. 8, line 5 | Delete rightside of formula and substitute |

-- 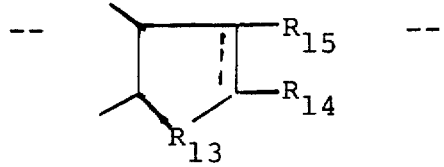 --

Signed and Sealed this

Sixteenth  Day of  April 1985

[SEAL]

*Attest:*

DONALD J. QUIGG

*Attesting Officer*   *Acting Commissioner of Patents and Trademarks*